(12) United States Patent
Stradella et al.

(10) Patent No.: US 8,186,343 B2
(45) Date of Patent: May 29, 2012

(54) DOSE INDICATOR FOR A FLUID DISPENSER DEVICE

(75) Inventors: Fabio Stradella, Camogli (IT);
Giuseppe Stradella, Camogli (IT)

(73) Assignee: Valois SAS, Le Neubourg (FR)

( * ) Notice: Subject to any disclaimer, the term of this patent is extended or adjusted under 35 U.S.C. 154(b) by 704 days.

(21) Appl. No.: 12/298,010

(22) PCT Filed: Apr. 23, 2007

(86) PCT No.: PCT/FR2007/051155
§ 371 (c)(1),
(2), (4) Date: Oct. 21, 2008

(87) PCT Pub. No.: WO2007/122358
PCT Pub. Date: Nov. 1, 2007

(65) Prior Publication Data
US 2009/0101150 A1    Apr. 23, 2009

(30) Foreign Application Priority Data

Apr. 24, 2006 (FR) ..................................... 06 51425

(51) Int. Cl.
*A61M 11/00* (2006.01)
(52) U.S. Cl. .......... 128/200.14; 128/200.15; 128/203.12
(58) Field of Classification Search .......... 128/200.11–200.24, 203.12, 203.15; 222/36, 38, 48, 162, 32, 33, 402, 13, 402.11; 116/285, 311, 312, 315, 308, 318; 604/58; 215/230; 206/459.1, 459.5
See application file for complete search history.

(56) References Cited

U.S. PATENT DOCUMENTS

| | | | | |
|---|---|---|---|---|
| 5,421,482 A * | 6/1995 | Garby et al. | ..................... | 222/36 |
| 6,082,358 A * | 7/2000 | Scarrott et al. | ........... | 128/205.23 |
| 7,191,918 B2 * | 3/2007 | Ouyang et al. | .................. | 222/36 |
| 7,464,708 B2 * | 12/2008 | Marx | ........................ | 128/205.23 |
| 7,780,038 B2 * | 8/2010 | Ingram et al. | .................... | 222/36 |
| 7,882,982 B2 * | 2/2011 | Stradella et al. | ................. | 222/38 |
| 2004/0149773 A1 * | 8/2004 | Ouyang et al. | .................. | 222/36 |

FOREIGN PATENT DOCUMENTS

| | | |
|---|---|---|
| EP | 1 386 630 A1 | 2/2004 |
| FR | 2 857 770 A1 | 1/2005 |
| WO | 98/52634 A1 | 11/1998 |
| WO | 03/028792 A1 | 4/2003 |
| WO | 2005/079727 A2 | 9/2005 |

* cited by examiner

*Primary Examiner* — Glenn Richman
(74) *Attorney, Agent, or Firm* — Sughrue Mion, PLLC

(57) ABSTRACT

A dose indicator for indicating the number of doses that have been dispensed or that remain to be dispensed from a fluid dispenser device, the indicator being characterized in that it comprises an indicator body, a drive element, a rotary transmission element, a first rotary counter element, and a second rotary counter element, said first and second rotary counter elements being disposed side by side in a common plane and turning about parallel axes of rotation, said first and second counter elements co-operating to provide a common indication on each occasion the indicator is driven, said first rotary counter element being a disk having a top surface and a bottom surface, said top surface including first indicator means located close to the outer peripheral edge of said top surface, and said bottom surface including a first gear co-operating with a drive gear provided on said rotary transmission element, said first rotary counter element including a drive tooth adapted to co-operate on each complete revolution of said first rotary counter element with a second gear provided on said second rotary counter element.

29 Claims, 3 Drawing Sheets

DOSE INDICATOR FOR A FLUID DISPENSER DEVICE

CROSS REFERENCE TO RELATED APPLICATION

This application is a National Stage of International Application No. PCT/FR2007/051155 filed Apr. 23, 2008, claiming priority based on French Patent Application No. 06.51425, filed Apr. 24, 2006, the contents of all of which are incorporated herein by reference in their entirety.

The present invention relates to a dose indicator, and also to a fluid dispenser device including such an indicator.

In the field of fluid dispenser devices for dispensing a plurality of doses, and in particular in the field of sprays, numerous systems have been developed for indicating the number of doses that have been dispensed or the number of doses that remain to be dispensed.

Most of those systems present numerous drawbacks. Thus, they are generally designed on the basis of numerous component parts that co-operate with one another. Consequently, such counters or indicators can become very complex and bulky, and they can therefore become expensive to fabricate and to assemble. Documents EP-1 386 630 and WO 2005/079727 describe such systems that are complex. Furthermore, indicator systems often include elastically-deformable elements for driving the system. Those elements can sometimes become deformed after a plurality of actuations, and they then no longer guarantee reliable operation of the system until the last dose. Document WO 98/52634 describes one such system. Furthermore, the indication is generally given as a number, and it is often difficult for the user to read, in particular when the dispenser device is designed to dispense a large number of doses, e.g. up to 200 doses. Another major drawback lies in the fact that existing counters generally require the procedure for assembling the dispenser device to be modified because of the presence of the counter, so that the procedure then differs from the usual assembly procedure. That increases the complexity of the device and consequently implies a cost that is greater.

Furthermore, a major safety requirement is to avoid any risk of under-counting, i.e. failing to count an occasion on which a dose of fluid has been dispensed in full or in part. In order to avoid that risk, it is necessary, during the stroke of the dispenser member, and in particular the valve member, for the counter to be driven before the fluid begins to be expelled. The length of this initial stroke is generally very short, typically of the order of 1 millimeter (mm) to 1.5 mm. The various dimensional tolerances for the device then reduce this stroke to a few tenths of a millimeter. Such a short drive stroke makes it difficult to operate the counter, and can imply using mechanisms that are complex in order to guarantee functional counting.

An object of the present invention is to provide a dose indicator for a fluid dispenser device that does not reproduce the above-mentioned drawbacks.

In particular, an object of the present invention is to provide a dose indicator that is simple and inexpensive to fabricate and assemble, that operates reliably until the last dose, and that is suitable in particular for being applied to any existing fluid dispenser device without requiring significant modification to the procedure for assembling it.

Another object of the present invention is to provide a dose indicator constituted by a small number of component parts, even if the number of doses contained in the dispenser device is high, e.g. 200 doses.

Another object of the present invention is to provider a dose indicator that forms a unit that is complete and separate and that includes in particular the means for driving the indicator.

Another object of the present invention is to provide a dose indicator that is easy for a user to read.

Another object of the present invention is to provide a dose indicator that avoids any risk of under-counting (failure to count a dose that has been dispensed). More particularly, an object of the present invention is to provide a dose indicator that counts at the beginning of the actuation stroke of the dispenser device with which it is associated, even if the initial stroke is very short.

The present invention thus provides a dose indicator for indicating the number of doses that have been dispensed or that remain to be dispensed from a fluid dispenser device, the indicator being characterized in that it comprises an indicator body, a drive element, a rotary transmission element, a first rotary counter element, and a second rotary counter element, said first and second rotary counter elements being disposed side by side in a common plane and turning about parallel axes of rotation, said first and second counter elements co-operating to provide a common indication on each occasion the indicator is driven, said first rotary counter element being a disk having a top surface and a bottom surface, said top surface including first indicator means located close to the outer peripheral edge of said top surface, and said bottom surface including a first gear co-operating with a drive gear provided on said rotary transmission element, said first rotary counter element including a drive tooth adapted to co-operate on each complete revolution of said first rotary counter element with a second gear provided on said second rotary counter element.

Advantageously, said first indicator means comprise digits, in particular the digits 0 to 9.

Advantageously, the second rotary counter element is a disk having a top surface and a bottom surface, said top surface including second indicator means disposed close to the outer peripheral edge of said top surface.

Advantageously, said second indicator means comprise numbers, in particular the numbers 00 to 20.

Advantageously, said bottom surface of said second rotary counter element includes a second gear co-operating with a drive tooth of said first rotary counter element.

Advantageously, said second rotary counter element includes a set of positioning teeth co-operating with a resilient tab of said drive element, in particular to ensure that said second rotary counter element is accurately positioned on each occasion it is turned.

Advantageously, said second rotary counter element includes stop means for preventing the indicator being driven after a predetermined number of indications, in particular 200.

Advantageously, said stop means comprise a projecting profile, such as a spur, secured to said second rotary counter element and co-operating with a stationary portion of the indicator body.

Advantageously, said rotary transmission element includes a first drive gear co-operating with said drive element, and a second drive gear co-operating with a first gear of said first rotary counter element.

Advantageously, said rotary transmission element is a disk having a top surface and a bottom surface, said bottom surface including said first drive gear and said top surface including said second drive gear.

Advantageously, said drive element includes anti-return means such as a resilient tab co-operating with said rotary transmission element to prevent it from turning in the direction opposite to the direction in which it turns when the indicator is driven.

Advantageously, said drive element includes a first resilient tab co-operating with a first drive gear of the rotary transmission element to cause said rotary transmission element to turn in the drive direction each time the indicator is driven, an anti-return, second resilient tab co-operating with said drive gear of the rotary transmission element to prevent any turning of said rotary transmission element in a direction opposite to said drive direction, and a third resilient tab co-operating with a set of positioning teeth of said second rotary counter element to ensure that said second rotary counter element is angularly positioned accurately each time it is turned.

Advantageously, said drive element includes a portion that is stationary relative to the indicator body, and a deformable portion adapted to co-operate with an actuation portion of a fluid dispenser device, said actuation portion being movable relative to said drive element over an actuation stroke.

Advantageously, said deformable portion of said drive element includes a first deformable portion having first flexibility and a second deformable portion having second flexibility, said second flexibility being less than said first flexibility.

Advantageously, said first deformable portion drives the indicator, and said more-rigid second deformable portion allows the actuation stroke of said actuator portion of the fluid dispenser device to be continued after said indicator has been driven.

Advantageously, said indicator is driven at the very beginning of the actuation stroke of said fluid dispenser device.

Advantageously, said actuation portion of the fluid dispenser device that co-operates with the deformable portion of the drive element is a fluid reservoir, said body of the indicator being stationary relative to the body of the fluid dispenser device.

Advantageously, said actuation portion of the fluid dispenser device that co-operates with the deformable portion of the drive element is a body of said fluid dispenser device, said body of the indicator being stationary relative to a fluid reservoir.

Advantageously, said indicator body includes a viewing window for displaying the common indication of said first and second rotary counter elements.

The present invention also provides a fluid dispenser device comprising a body, a reservoir movable over an actuation stroke relative to said body, and an inhalation endpiece, together with an indicator as described above.

These and other characteristics and advantages of the present invention appear more clearly from the following detailed description of a particular embodiment thereof, made with reference to the accompanying drawings, given non-limiting examples, and in which.

The dose indicator A of the present invention applies to all types of fluid dispenser device. Nevertheless, it applies more particularly to spray devices, and advantageously to aerosol inhaler devices of the kind that includes a metering valve mounted on a receptacle that contains a fluid and a propellant gas.

Figure 1:
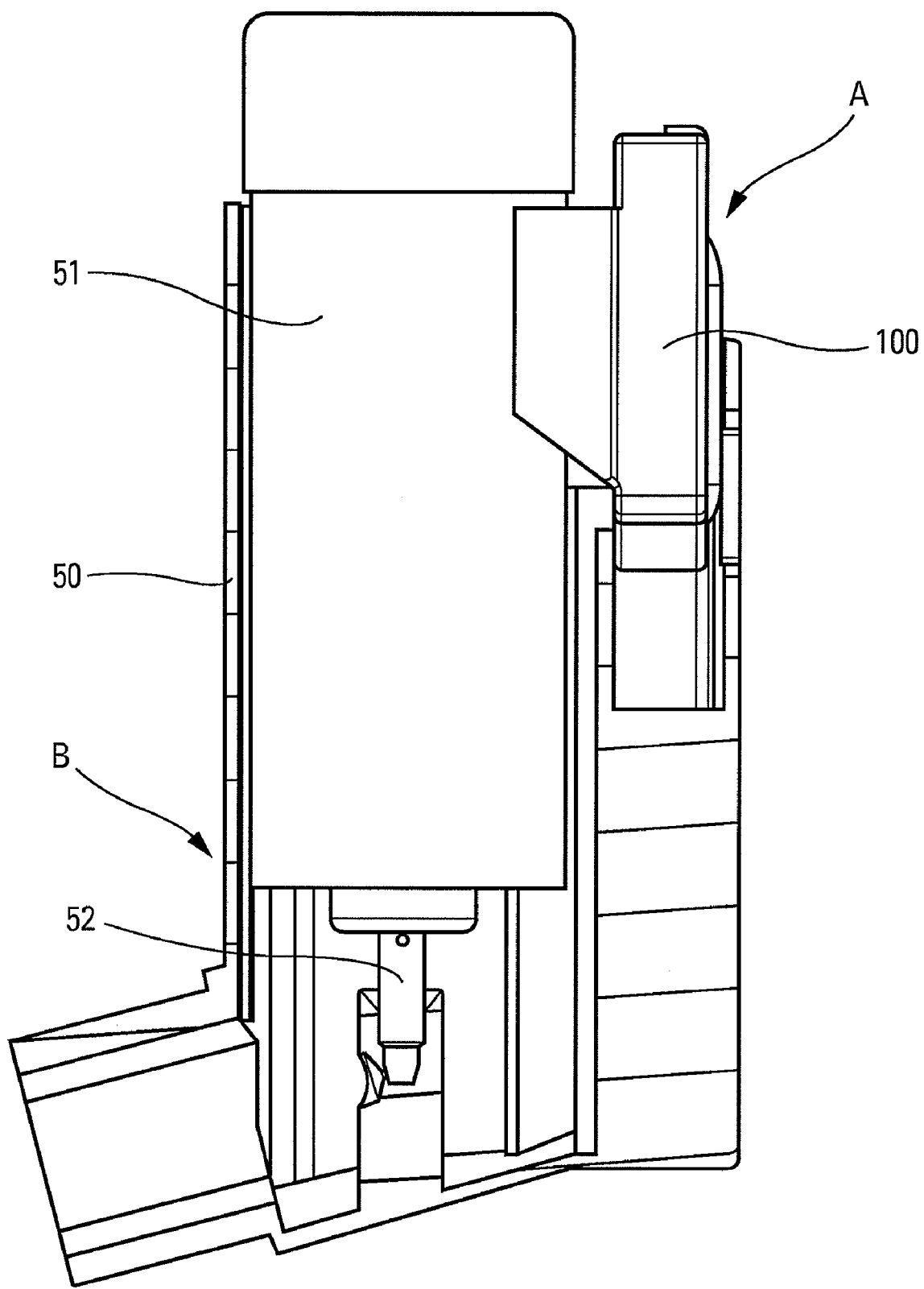
FIG. 1 is a diagrammatic side view of a fluid dispenser device (B) including a dose indicator (A) constituting an advantageous embodiment of the present invention.

FIG. 1 is a diagram of a dispenser device B for which the dose indicator A of the present invention is particularly adapted. The device comprises a body 50 and a reservoir 51 having a metering valve 52 assembled thereon. Actuation of the device B is obtained by axially moving the reservoir 51 inside the body 50 over an actuation stroke, this movement causing the valve member of the valve 52 to be compressed, thereby causing a dose of fluid to be expelled through a mouthpiece 55. Naturally, the present invention also applies to other types of dispenser device, and in particular to nasal type spray devices or to devices that include a pump instead of the valve. In the example shown, the indicator A is fastened to the reservoir 51 in any suitable manner. It could nevertheless be positioned differently or it could be fastened to the body 50 of the device.

FIGS. 2 to 7 show a dose indicator A that can be used in particular with a fluid dispenser device B as described above. The dose indicator comprises an indicator body 100 containing an actuator element 1, a rotary transmission element 7, a first rotary counter element 13, and a second rotary counter element 10. Advantageously, the indicator body 100 includes a cover that incorporates a viewing window through which the user can view the indication of the indicator A. The indicator of the present invention thus comprises only four deformable and/or moving parts.

According to the invention, the first rotary counter element 1 and the second rotary counter element 10 are placed side by side in a common plane and they turn about parallel axes of rotation such that first and second rotary counter elements 13, 10 co-operate to provide a common indication on each actuation.

Figure 5:
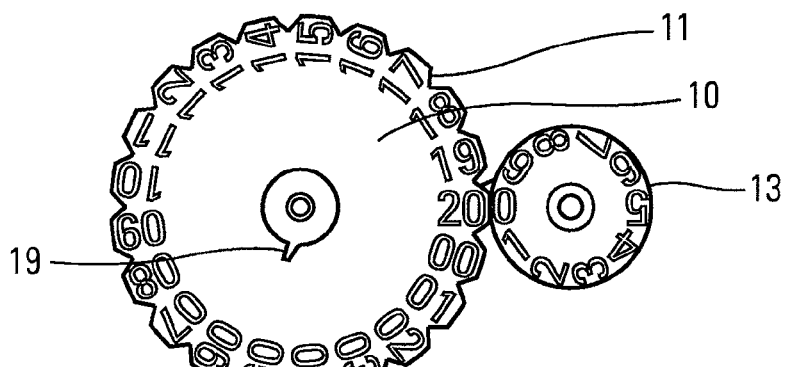
FIG. 5 is a diagrammatic plan view of two rotary counter elements, together indicating a count of 200.

FIG. 5 shows in particular the starting position of an indicator adapted to count the number of doses remaining within the reservoir 51, where the maximum number of doses is equal to 200. Thus, with reference to FIG. 5, the common indication provided by the first and second rotary counter elements 13, 10 forms the number 200, which can then be seen through the viewing window in the indicator body 100.

As can be seen in the figures, the first rotary counter element 13 can be made in the form of a disk having a top surface and a bottom surface, the top surface including first indicator means disposed near an outer peripheral edge of said top surface, while the bottom surface includes a first gear 16. Similarly, the second rotary counter element 10 may also be formed as a disk having a top surface and a bottom surface, said top surface having second indicator means, advantageously disposed near the outer peripheral edge of said top surface, and said bottom surface including a second gear 12.

Preferably, when the indicator is for counting 200 doses, the first rotary counter element 13 includes the digits 0 to 9 distributed around its periphery, whereas the second rotary counter element includes the numbers 00 to 20 likewise distributed around its periphery, as can be seen in FIG. 5.

Advantageously, the first and second rotary counter elements 13, 10 turn about axes of rotation that are secured to the cover of the indicator body 100.

Figure 6:
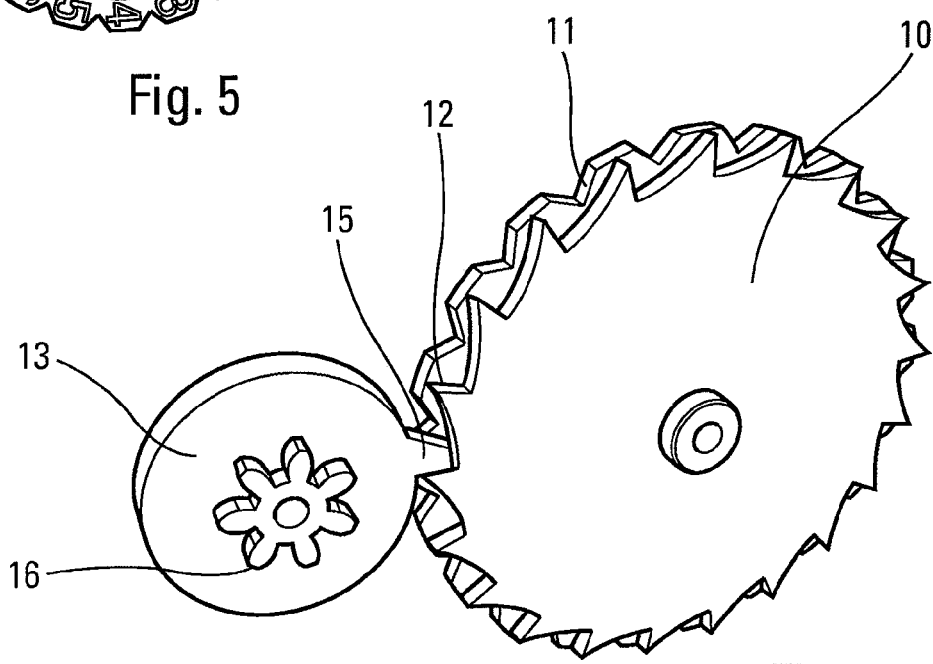
FIG. 6 is a view similar to the view of FIG. 5, seen from beneath.
Figure 7:
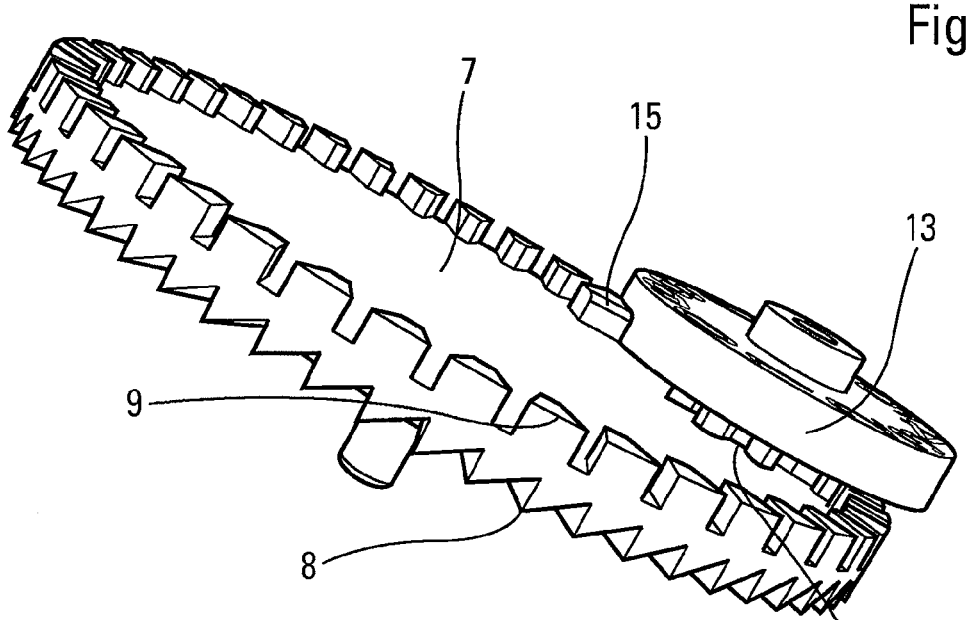
FIG. 7 is a diagrammatic perspective view of the rotary transmission element and of the first rotary counter element.

Behind the first and second rotary counter elements 13, 10, where "behind" is relative to the viewing direction of a user, there is located the rotary transmission element 7. This rotary transmission element 7 is also preferably made in the form of a disk having a top surface and a bottom surface. The bottom surface preferably includes a first drive gear 8, and the top surface advantageously includes a second drive gear 9. The second drive gear 9 is suitable for co-operating with the first gear 16 of the first rotary counter element 13. This can be seen in particular in FIGS. 2 and 7. Thus, on each rotation of the rotary transmission element 7, there is a corresponding rotation of the first rotary counter element 13. As can be seen in FIG. 6, the first rotary counter element 13 has a drive tooth 15 adapted to co-operate on each complete revolution of the first rotary counter element 13 with the second gear 12 provided on said second rotary counter element 10. Thus, each time the first rotary counter element 13 makes a complete revolution, it turns the second rotary counter element 10. In this configuration, the first rotary counter element corresponds to indicating units (from 0 to 9), while the second rotary counter element 10 corresponds to indicating tens (from 00 to 20). The indicator shown in the drawings thus enables 200 doses to be counted.

Figure 2:
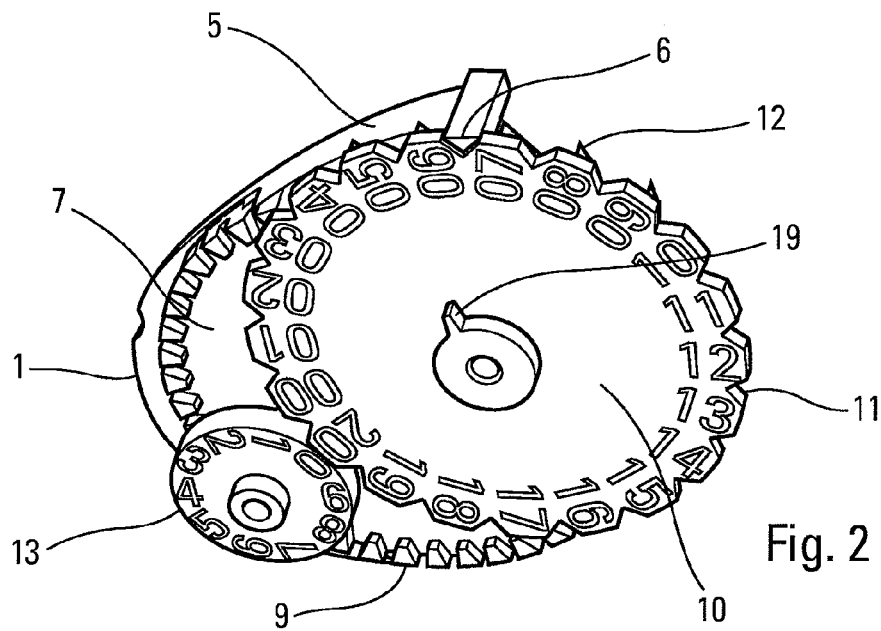
FIG. 2 is a diagrammatic perspective view of a portion of a dose indicator in an advantageous embodiment of the invention.
Figure 3:
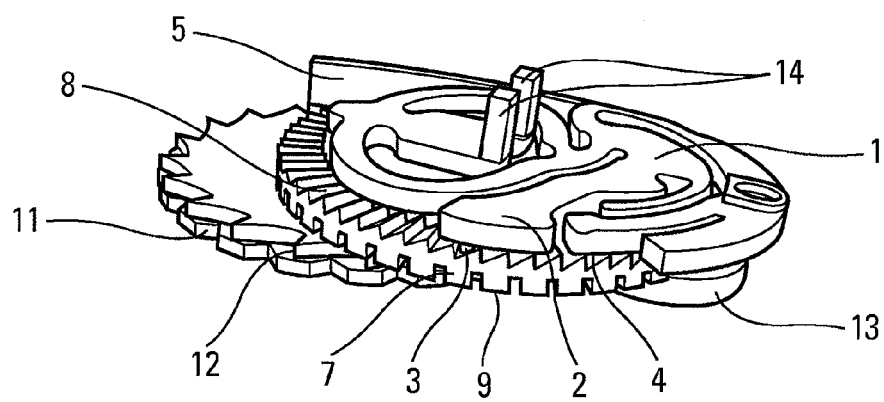
FIG. 3 is a view similar to the view of FIG. 2, from a different viewing angle.
Figure 4:
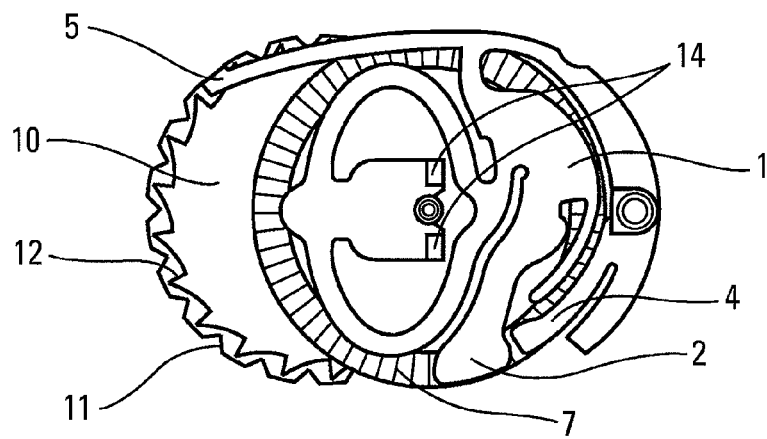
FIG. 4 is a view similar to the view of FIG. 3, from yet another viewing angle.

Advantageously, the second rotary counter element 10 also includes stop means 19, in particular implemented in the form of a projecting profile such as a spur, and that can be secured to said second rotary counter element 10, as can be seen in particular in FIG. 2. The spur 19 is adapted to co-operate with a stationary portion of the indicator body 100 after some predetermined number of indications, and in particular after 200 indications for the indicator shown in the drawings. The spur 19 thus serves to prevent the indicator continuing to operate once the maximum number of doses has been counted.

Behind the rotary transmission element 7, where "behind" is relative to the viewing direction of a user, there is located a drive element 1. This drive element 1 co-operates firstly with a moving portion (that moves relative to said drive element) of the fluid dispenser device B (see in particular FIG. 1), and secondly it is adapted to drive said rotary transmission element 7 to turn on each occasion that the device is actuated. The operation of this drive element 1 is described in greater detail below.

In simplified manner, the drive element 1 comprises a portion that is stationary relative to the body 100 of the indicator A, and a portion that is deformable. When the user actuates the dispenser device B, in particular by pushing the reservoir 51 into the body 50 in the context of a device B as shown in FIG. 1, that deforms the deformable portion of the drive element 1, with this deformation causing the rotary transmission element 7 to turn, thereby in turn causing the first rotary counter element 13 to turn. Advantageously, the drive element 1 has a first flexible tab 2 adapted to co-operate with the first drive gear 8 provided on the rotary transmission element 7 to cause said rotary transmission element 7 to turn in the drive direction each time the indicator is actuated. Furthermore, the drive element 1 also advantageously includes a second flexible tab 4 for preventing return, that also preferably co-operates with said first drive gear 8 of the rotary transmission element 7 to ensure that said rotary transmission element 7 cannot turn in the opposite direction relative to said drive direction. Finally, the drive element 1 may advantageously include a third flexible tab 5 adapted to co-operate with a set of positioning teeth 11 made on the second rotary counter element 10 so as to ensure that said second rotary counter element 10 occupies an accurate angular position each time it is turned. This set of positioning teeth 11 can be seen more clearly in FIG. 2, where the third flexible tab 5 is shown provided at its end with a tooth 6 that meshes in said peripheral set of positioning teeth 11 formed in the side edge of said second rotary counter element 10.

In order to enable the actuation stroke of the fluid dispenser device to continue after the indicator has been driven, the drive element 1 includes a first flexible portion having first flexibility and a second flexible portion having second flexibility less than the first flexibility. In other words, the first flexible portion, which incorporates the first flexible tab 2 that drives the indicator A, is actuated as soon as the drive element 1 is deformed during actuation of the device. Once the indicator has been actuated, continuing the actuation stroke is made possible by the more rigid second flexible portion that deforms only after the indicator has been driven.

Thus, drive of the indicator A, and in particular turning of the rotary transmission element 7 is advantageously performed by the drive element 1 that is integrated in said indicator A. This drive element 1 may include a first flexible tab 2 adapted to co-operate with said first drive gear each time a dose is dispensed, with this co-operation preferably taking place via at least one drive member 3 such as a tooth.

The drive element 1 also includes a transmission element 14 that is adapted to co-operate with the fluid dispenser device B each time it is actuated. In particular, and as can be seen more particularly in FIG. 3, said transmission element 14 may have one or more shoulders secured to the drive element 1 and co-operating with the actuator portion 50, 51 of the fluid dispenser device B that is moved relative to the drive element 1 during actuation. In the example shown, this is constituted by a portion of the body 50. Naturally, and more generally, any portion that moves relative to the drive element 1 during actuation of the device B can be adapted to co-operate with the shoulders 14 in order to drive the dose indicator A. Thus, if the body 100 of the indicator A is fastened to the reservoir 51, then a portion that is stationary relative to the body 50 could co-operate with the drive element 1. In contrast, if the body 100 of the indicator A is fastened relative to the body 50, then the reservoir 51, or any portion secured thereto, could co-operate with the drive element 1.

The drive element 1 may be provided with two flexible portions having different flexibilities, the first flexible portion being more flexible than the second flexible portion. This more-rigid, second flexible portion supports said shoulders 14, and when the dispenser device B is actuated, a portion of the actuation of the dispenser device B begins by entraining the more-flexible, first portion that comprises the first flexible tab 2, causing it to bend relative to the rotary transmission element 7, which in turn causes said rotary transmission element 7 to turn by means of the tooth 3 co-operating with the first drive gear 8. Advantageously, the first flexible tab 2 can also co-operate with stop means adapted to prevent the first flexible tab 2 moving after moving the equivalent of one tooth of the first drive gear 8. Thus, during actuation, the shoulders 14 are moved by the dispenser device B, and the first flexible tab 2 bends until the first flexible tab 2 comes into contact with the stop means. This causes the rotary transmission element 7 to turn through the equivalent of one tooth. The first flexible tab 2 is then blocked, and it is possible to continue the actuation stroke of the dispenser device B by bending the more rigid second portion of the drive element 1. This enables the dose indicator A to be driven at the very beginning of said actuation stroke. This eliminates any risk of a dose that is dispensed (whether in full or in part) failing to be counted in the event of the dispenser device B being actuated only partially, while also allowing the actuation stroke to be continued after counting has taken place. The anti-return means 4 ensure that each dose is counted only once.

The number of teeth in the various gears defines the characteristics of the dose indicator, and in particular the number of doses that the indicator can count. The maximum number of doses and the way in which they are displayed can be varied at will by modifying the indicator means or the number of teeth of one or more of the gears. The present invention thus enables dose indicators to be made that are adapted to counting an arbitrary number of doses, without modifying the shape or the size of said indicator. As mentioned above, the structural dimensions of the present indicator are particularly small, in particular in the thickness direction, and the indicator A can therefore be incorporated very easily in existing fluid dispenser devices B, as can be seen in FIG. 1.

The dose indicator of the present invention enables the number of doses dispensed or the number of doses that remain for dispensing in the device to be viewed in a manner that is simple, inexpensive, and progressive. The structure of the indicator is thin, independently of the number of doses it needs to indicate, and it does not have any projecting portion that would require a modification of the device to which it is applied. As can be seen in FIG. 1, the dose indicator A of the present invention can be applied very easily to any existing device, without the device needing to be modified. In addition, the presence of the indicator A does not modify the process of assembling the device B. By way of example, the indicator may be fastened to the reservoir 51 by any suitable means. Another advantage of the present indicator is that the indicator drive means are incorporated therein, such that the indicator forms a self-contained and separate unit that can be preassembled, and that can easily be incorporated in any fluid dispenser device. The dose indicator of the present invention serves above all to guarantee that said indicator is driven at the very beginning of the actuation stroke, in particular during the initial stroke that takes place prior to the beginning of dose expulsion. Furthermore, the indicator of the invention is simple and reliable, and has only four deformable and/or rotary parts.

Naturally, the present invention is described with reference to a particular embodiment thereof, as shown in the drawings, however the invention is not limited to that particular embodiment. On the contrary, a person skilled in the art can apply any modification thereto without going beyond the ambit of the present invention as defined in the accompanying claims.

The invention claimed is:

1. A dose indicator for indicating the number of doses that have been dispensed or that remain to be dispensed from a fluid dispenser device, the indicator comprising an indicator body, a drive element, a rotary transmission element, a first rotary counter element, and a second rotary counter element, said first and second rotary counter elements disposed side by side in a common plane and turning about parallel axes of rotation, said first and second counter elements co-operating to provide a common indication on each occasion the indicator is driven, said first rotary counter element is a disk having a top surface and a bottom surface, said top surface including first indicator means located close to the outer peripheral edge of said top surface, and said bottom surface including a first gear co-operating with a drive gear provided on said rotary transmission element, said first rotary counter element including a drive tooth adapted to co-operate on each complete revolution of said first rotary counter element with a second gear provided on said second rotary counter element;

said drive element includes a portion that is stationary relative to the indicator body, and a deformable portion adapted to co-operate with an actuation portion of a fluid dispenser device, said actuation portion movable relative to said drive element over an actuation stroke; and said actuation portion of the fluid dispenser device that co-operates with the deformable portion of the drive element is a fluid reservoir, said body of the indicator being stationary relative to the body of the fluid dispenser device.

2. The indicator according to claim 1, wherein said first indicator means comprise digits.

3. The indicator according to claim 1, wherein the second rotary counter element is a disk having a top surface and a bottom surface, said top surface including second indicator means disposed close to the outer peripheral edge of said top surface.

4. The indicator according to claim 3, wherein said second indicator means comprise numbers.

5. The indicator according to claim 3, wherein said bottom surface of said second rotary counter element includes a second gear co-operating with a drive tooth of said first rotary counter element.

6. The indicator according to claim 1, wherein said second rotary counter element includes a set of positioning teeth co-operating with a resilient tab of said drive element to ensure that said second rotary counter element is accurately positioned on each occasion said second rotary counter element is turned.

7. The indicator according to claim 1, wherein said second rotary counter element includes stop means for preventing the indicator from being driven after a predetermined number of indications.

8. The indicator according to claim 7, wherein said stop means comprise a projecting profile, such as a spur, secured to said second rotary counter element and co-operating with a stationary portion of the indicator body.

9. The indicator according to claim 1, wherein said rotary transmission element includes a first drive gear co-operating with said drive element, and a second drive gear co-operating with a first gear of said first rotary counter element.

10. The indicator according to claim 9, wherein said rotary transmission element is a disk having a top surface and a bottom surface, said bottom surface including said first drive gear and said top surface including said second drive gear.

11. The indicator according to claim 1, wherein said drive element includes anti-return means to prevent said rotary transmission element from turning in the direction opposite to the direction in which said rotary transmission element turns when the indicator is driven.

12. The indicator according to claim 1, wherein said drive element includes a first resilient tab co-operating with a first drive gear of the rotary transmission element to cause said rotary transmission element to turn in the drive direction each time the indicator is driven, an anti-return, second resilient tab co-operating with said drive gear of the rotary transmission element to prevent any turning of said rotary transmission element in a direction opposite to said drive direction, and a third resilient tab co-operating with a set of positioning teeth of said second rotary counter element to ensure that said second rotary counter element is angularly positioned accurately each time said second rotary counter element is turned.

13. The indicator according to claim 1, wherein said indicator is driven at the very beginning of the actuation stroke of said fluid dispenser device.

14. The indicator according to claim 1, wherein said indicator body includes a viewing window for displaying the common indication of said first and second rotary counter elements.

15. A fluid inhaler device comprising a body, a reservoir movable over an actuation stroke relative to said body, and an inhalation endpiece, the device comprising an indicator according to claim 1.

16. The indicator according to claim 2, wherein the digits are 0 to 9.

17. The indicator according to claim 4, wherein the numbers are 00 to 20.

18. The indicator according to claim 7, wherein the predetermined number of indications is 200.

19. The indicator according to claim 11, wherein the anti-return means comprises a resilient tab co-operating with said rotary transmission element.

20. A dose indicator for indicating the number of doses that have been dispensed or that remain to be dispensed from a fluid dispenser device, the indicator comprising an indicator body, a drive element, a rotary transmission element, a first rotary counter element, and a second rotary counter element, said first and second rotary counter elements disposed side by side in a common plane and turning about parallel axes of rotation, said first and second counter elements co-operating to provide a common indication on each occasion the indicator is driven, said first rotary counter element is a disk having a top surface and a bottom surface, said top surface including first indicator means located close to the outer peripheral edge of said top surface, and said bottom surface including a first gear co-operating with a drive gear provided on said rotary transmission element, said first rotary counter element including a drive tooth adapted to co-operate on each complete revolution of said first rotary counter element with a second gear provided on said second rotary counter element;
said drive element includes a portion that is stationary relative to the indicator body, and a deformable portion adapted to co-operate with an actuation portion of a fluid dispenser device, said actuation portion movable relative to said drive element over an actuation stroke;
said deformable portion of said drive element includes a first deformable portion having first flexibility and a second deformable portion having second flexibility, said second flexibility being less than said first flexibility; and
said first deformable portion drives the indicator, and said more-rigid second deformable portion allows the actuation stroke of said actuator portion of the fluid dispenser device to be continued after said indicator has been driven.

21. A dose indicator for indicating the number of doses that have been dispensed or that remain to be dispensed from a fluid dispenser device, the indicator comprising an indicator body, a drive element, a rotary transmission element, a first rotary counter element, and a second rotary counter element, said first and second rotary counter elements disposed side by side in a common plane and turning about parallel axes of rotation, said first and second counter elements co-operating to provide a common indication on each occasion the indicator is driven, said first rotary counter element is a disk having a top surface and a bottom surface, said top surface including first indicator means located close to the outer peripheral edge of said top surface, and said bottom surface including a first gear co-operating with a drive gear provided on said rotary transmission element, said first rotary counter element including a drive tooth adapted to co-operate on each complete revolution of said first rotary counter element with a second gear provided on said second rotary counter element;
said drive element includes a portion that is stationary relative to the indicator body, and a deformable portion adapted to co-operate with an actuation portion of a fluid dispenser device, said actuation portion movable relative to said drive element over an actuation stroke; and
said actuation portion of the fluid dispenser device that co-operates with the deformable portion of the drive element is a body of said fluid dispenser device, said body of the indicator being stationary relative to a fluid reservoir.

22. The indicator according to claim 21, wherein said first indicator means comprise digits.

23. The indicator according to claim 21, wherein the second rotary counter element is a disk having a top surface and a bottom surface, said top surface including second indicator means disposed close to the outer peripheral edge of said top surface.

24. An The indicator according to claim 21, wherein said second rotary counter element includes a set of positioning teeth co-operating with a resilient tab of said drive element to ensure that said second rotary counter element is accurately positioned on each occasion said second rotary counter element is turned.

25. The indicator according to claim 21, wherein said second rotary counter element includes stop means for preventing the indicator being driven after a predetermined number of indications.

26. The indicator according to claim 21, wherein said rotary transmission element includes a first drive gear co-operating with said drive element, and a second drive gear co-operating with a first gear of said first rotary counter element.

27. The indicator according to claim 21, wherein said drive element includes anti-return means to prevent said rotary transmission element from turning in the direction opposite to the direction in which said rotary transmission element turns when the indicator is driven.

28. A fluid inhaler device comprising a body, a reservoir movable over an actuation stroke relative to said body, and an inhalation endpiece, the device comprising an indicator according to claim 21.

29. A dose indicator for indicating the number of doses that have been dispensed or that remain to be dispensed from a fluid dispenser device, the indicator comprising an indicator body, a drive element, a rotary transmission element, a first rotary counter element, and a second rotary counter element, said first and second rotary counter elements disposed side by side in a common plane and turning about parallel axes of rotation, said first and second counter elements co-operating to provide a common indication on each occasion the indicator is driven, said first rotary counter element is a disk having a top surface and a bottom surface, said top surface including first indicia means located close to the outer peripheral edge of said top surface, and said bottom surface including a first gear co-operating with a drive gear provided on said rotary transmission element, said first rotary counter element including a drive tooth adapted to co-operate on each complete revolution of said first rotary counter element with a second gear provided on said second rotary counter element;
said drive element includes a first resilient tab co-operating with a first drive gear of the rotary transmission element to cause said rotary transmission element to turn in the drive direction each time the indicator is driven, an anti-return, second resilient tab co-operating with said drive gear of the rotary transmission element to prevent turning of said rotary transmission element in a direction opposite to said drive direction, and a third resilient tab co-operating with a set of positioning teeth of said second rotary counter element to ensure that said second rotary counter element is angularly positioned accurately each time said second rotary counter element is turned.

* * * * *